(12) United States Patent
Botte

(10) Patent No.: US 11,717,273 B1
(45) Date of Patent: Aug. 8, 2023

(54) SYSTEM, METHOD AND APPARATUS FOR TEST KIT FOR RAPID VIRAL DIAGNOSTIC SENSOR

(71) Applicant: Texas Tech University System, Lubbock, TX (US)

(72) Inventor: Gerardine G. Botte, Lubbock, TX (US)

(73) Assignee: Texas Tech University System, Lubbock, TX (US)

( * ) Notice: Subject to any disclaimer, the term of this patent is extended or adjusted under 35 U.S.C. 154(b) by 0 days.

(21) Appl. No.: 17/735,866

(22) Filed: May 3, 2022

(51) Int. Cl.
*A61B 10/00* (2006.01)
*A61B 1/005* (2006.01)

(52) U.S. Cl.
CPC ........ *A61B 1/0051* (2013.01); *A61B 10/0096* (2013.01)

(58) Field of Classification Search
CPC ............ A61B 10/0051; A61B 10/0096; G01N 27/30; G01N 33/487
See application file for complete search history.

(56) References Cited

U.S. PATENT DOCUMENTS

| 5,380,650 A * | 1/1995 | Barnard | G01N 33/533 548/312.1 |
| 11,060,995 B1 | 7/2021 | Botte et al. | |
| 2015/0124248 A1* | 5/2015 | Tipper | G01N 15/06 356/243.2 |
| 2022/0018797 A1 | 1/2022 | Botte et al. | |

OTHER PUBLICATIONS

Gubalane, Plant Pigments, Mar. 25, 2017, ReviewEssays, entire document (Year: 2017).*

* cited by examiner

*Primary Examiner* — Jill A Warden
*Assistant Examiner* — John McGuirk
(74) *Attorney, Agent, or Firm* — Dickinson Wright PLLC; Kristopher Lance Anderson

(57) ABSTRACT

A kit for testing for a virus and interacting with a sensor are disclosed. For example, the kit can include a first container having a first media for conditioning, catalyst formation and rinsing of the sensor. The first media can comprise V mL of 1 M KOH. The kit can have a second container with a second media for negative control (baseline solution) for the sensor. The second media can comprise W ML of 0.01 M KOH. The kit can further include a third container having a third media for sample testing with the sensor. The third media can comprise X mL of 0.01 M KOH. The third container can receive Y mL of saliva to complete a Z mL total volume in the third container prior to sample testing. In some versions, a ratio V: W: X: Y: Z=1.0: 1.0: 0.9: 0.1: 1.0 can be used.

6 Claims, 3 Drawing Sheets

SYSTEM, METHOD AND APPARATUS FOR TEST KIT FOR RAPID VIRAL DIAGNOSTIC SENSOR

CROSS-REFERENCE TO RELATED APPLICATION

None.

BACKGROUND

Field of the Disclosure

The present disclosure relates in general to the field of pathogen detection technologies. In particular, a test kit is provided for rapid detection of airborne viruses and virions. The kit and method for rapid detection of viruses and virions such as for detection in the novel coronavirus (SARS-CoV-2) and related products and services.

Description of the Prior Art

With the total number of confirmed cases related to SARS-CoV-2 crossing the 6 million mark, along with the death of over 430,000 infected individuals (as per the Coronavirus Resource Center of Johns Hopkins University), it is critical to ensure early detection of individuals affected by the virus. Techniques like the quantitative reverse transcriptase polymerase chain reaction (qRT-PCR) require hours before they can confirm the presence or absence of the virus in a sample.

Moreover, with the cases increasing exponentially, it can only be foreseen that there would be a lot more samples to be tested and this could potentially cause a delay in valuable time. The requirement for point-of-care detection devices are of high significance now more than ever. Such devices can be deployed anywhere starting from hospitals, clinical laboratories to airports, grocery stores and other places where there are people still gathering for basic needs. Apart from these places, if such devices are feasible to be manufactured in bulk, they can be used by the people staying at home in isolation to check themselves for exposure to the virus by following a standard operating procedure. Although some existing solutions are workable, improvements in testing continue to be of interest.

SUMMARY

Embodiments of a kit for testing for a virus and interacting with a sensor are disclosed. For example, the kit can include a first container (T1) having a first media for conditioning, catalyst formation and rinsing of the sensor. The first media can comprise V mL of 1 M KOH. The kit can have a second container (T2) with a second media for negative control (baseline solution) for the sensor. The second media can comprise W ML of 0.01 M KOH. The kit can further include a third container (T3) having a third media for sample testing with the sensor. The third media can comprise X mL of 0.01 M KOH. The T3 can be configured to receive Y mL of saliva to complete a Z mL total volume in the T3 prior to sample testing. In some versions, a ratio V: W: X: Y: Z=1.0: 1.0: 0.9: 0.1: 1.0 can be used. In addition, a rack R can retain and support T1, T2 and T3, in some examples, which can be color coded.

Other embodiments of the kit can include the first container (T1) having the first media for conditioning, catalyst formation and rinsing of the sensor. The first media can comprise 2 mL of 1 M KOH. The kit can have the second container (T2) with the second media for negative control (baseline solution) for the sensor. The second media can comprise 2 ML of 0.01 M KOH. The third container (T3) can have the third media for sample testing with the sensor. The third media can comprise 1.8 mL of 0.01 M KOH. T3 can be configured to receive 0.2 mL of saliva to complete a 2.0 mL total volume in the T3 prior to sample testing.

Still other embodiments can comprise a method of using the kit with a device for testing for a virus. The method can include providing a rack of containers T1, T2, T3, each having a media comprising KOH; adding saliva to T3 to form a test sample; placing T1, T2, T3 in the device; probing the media of T1 with a sensor of the device and forming a catalyst therein; probing the media of T2 with the sensor to calibrate the device; probing the media of T3 with the sensor to determine if a virus is present; and again probing the media of T1 with the sensor to rinse and clean the sensor for a next test sample with no additional cleaning step.

BRIEF DESCRIPTION OF THE DRAWINGS

Before one or more embodiments are described in detail, one skilled in the art will appreciate that they are not limited in its application to the details of construction, the arrangements of components, and the arrangement of steps set forth in the following detailed description or illustrated in the drawings and descriptions. Rather, they are capable of other embodiments and of being practiced or being carried out in various ways. Also, it is to be understood that the phraseology and terminology used herein is for the purpose of description and should not be regarded as limiting.

DETAILED DESCRIPTION

Figure 1:
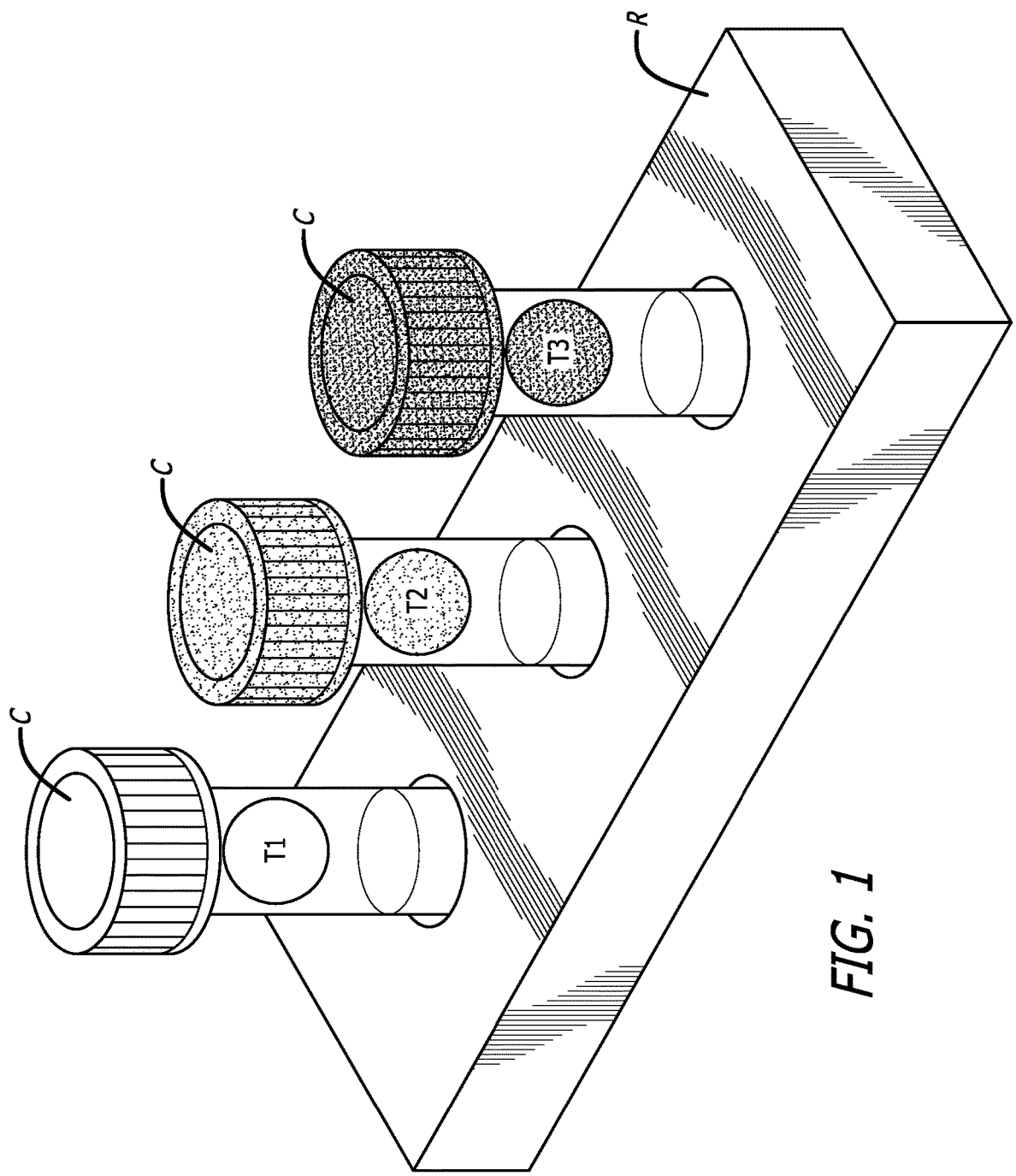
FIG. 1 is a perspective view of an embodiment of a kit.

The following descriptions of various implementations of the present teachings have been presented for purposes of illustration and description. It is not exhaustive and does not limit the present teachings to the precise form disclosed. Modifications and variations are possible in light of the above teachings or may be acquired from practicing of the present teachings.

The coronavirus disease (COVID-19) pandemic has created both a public health crisis and an economic crisis in the United States and around the world. As of the drafting of this disclosure, the rapidly rising number of cases globally of COVID-19 was in excess of 500,000,000 with a death toll of over 6,000,000 around the world. From an economic perspective, the United States experienced two consecutive quarters of declines in gross domestic product (GDP) and record hikes in unemployment due to economic shutdowns compelled by the pandemic. Since its first detection in China, COVID continues to spread with new variants emerging.

Detection of the virus in people is important for treating the sufferer and for slowing the spread of the disease. Likewise, environmental detection of the virus could contribute to methods for controlling and slowing the spread of the virus according to public health experts. There are several diagnostic methods for detecting the coronavirus in clinical, research, and public health laboratories. There also are methods for detecting the virus in environmental samples. Some studies suggest that increases in SARS-CoV-2 RNA can be detected in environmental samples several days before detection of COVID-19 through clinical surveillance methods, which could potentially lead to an early warning system for the presence of the virus in the environment.

This disclosure describes a test kit and method for a sampling and testing system for SARS-CoV-2 that is described in the patent U.S. Pat. No. 11,060,995, which is incorporated herein by reference in its entirety. The capability of the test kit and that system will significantly contribute to reducing the spread of the virus and human infections from this and future pathogenic threats.

The products of this disclosure will compete generally with traditional chemical and biochemical sensing platforms as well as sensing platforms for environmental pathogens. Public health experts have emphasized the importance of testing, tracking infected people, and tracing their contacts as an effective strategy to reduce the spread of the virus. As mentioned previously, there are existing methods for detecting the virus in environmental samples. There are also different types of bio-aerosol sampling including passive and active sampling that enable capturing and testing of airborne viruses like COVID-19 that are based on collecting samples obtained from air filters a performing RT-PCR.

Rather than testing the SARS-CoV-2 proteins in phosphate buffer saline (PBS), an approach was made to test samples in a close-to-reality scenario wherein the sample collection was non-invasive (extends the applicability of the sensor as sample collection is easier). There are reports in the literature that up to 91.7% (11 out of 12) patients host detectable virus in saliva. Hence, for an exemplary embodiment a sample collection was a like field scenario where protein concentration of interest was mixed to 3 mL of medical-grade artificial saliva mixed with PBS and 1N potassium hydroxide solution (KOH) (commercial standardized solution) in a final volume of 20 mL to achieve a pH of 12. At such high pH, it is expected that cells and viruses will lyse and release proteins in solution. Therefore, present example benefited from the use of recombinant viral proteins. For this exemplary embodiment, two different concentrations of protein S1 of SARS-CoV-2 were tested in artificial saliva solution and the results are disclosed in U.S. Pat. No. 11,060,995. A clear distinction in current between the baseline (no protein) curve, and 10 μg and 30 μg of protein can be observed, meaning the protein in the solution has been detected. Even between the two different concentrations, there is a clear separation concluding the sensor of the present invention can be used to quantitatively detect coronavirus in saliva samples.

Figure 2:
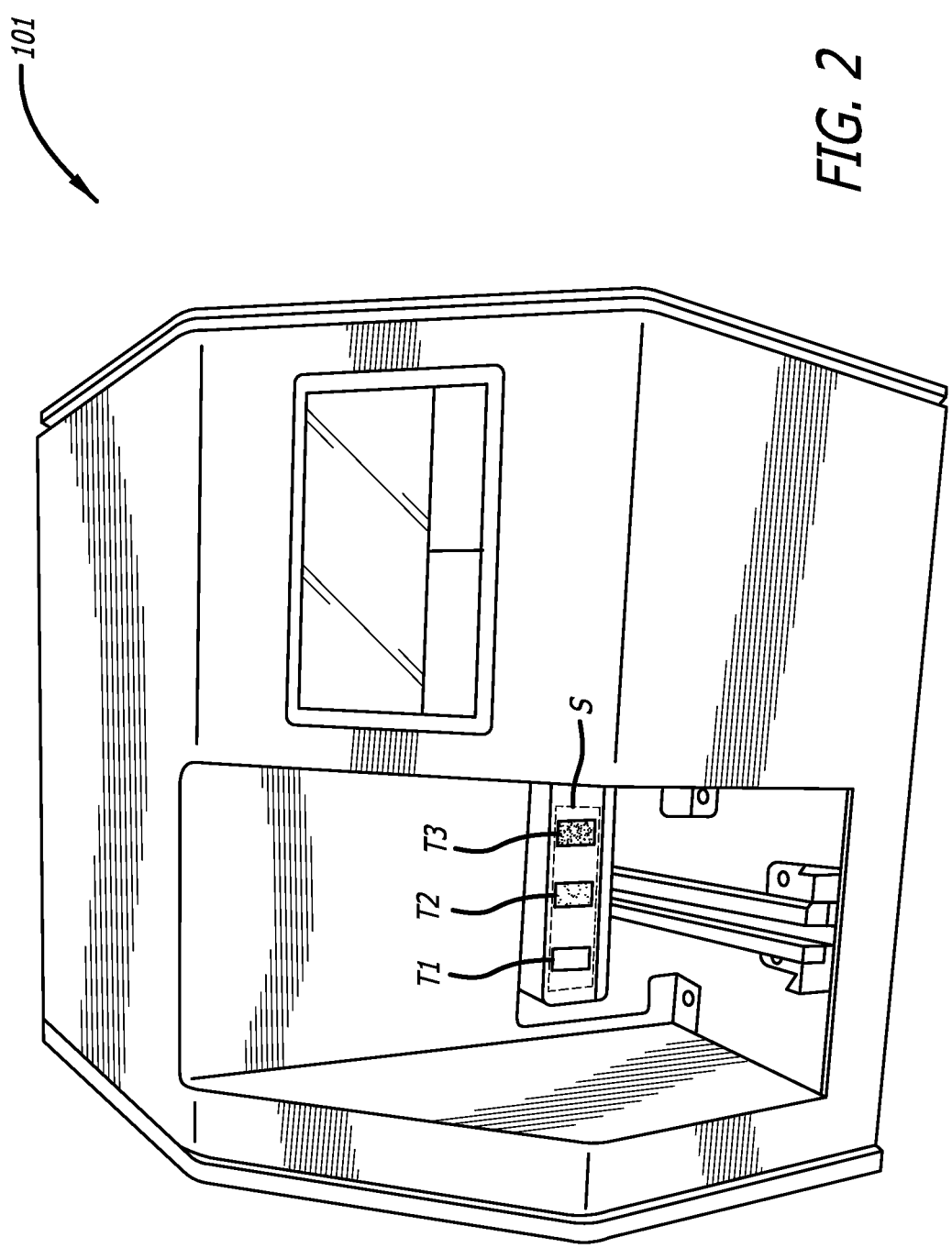
FIG. 2 is a perspective view of an embodiment of the kit being tested in a machine.
Figure 3:
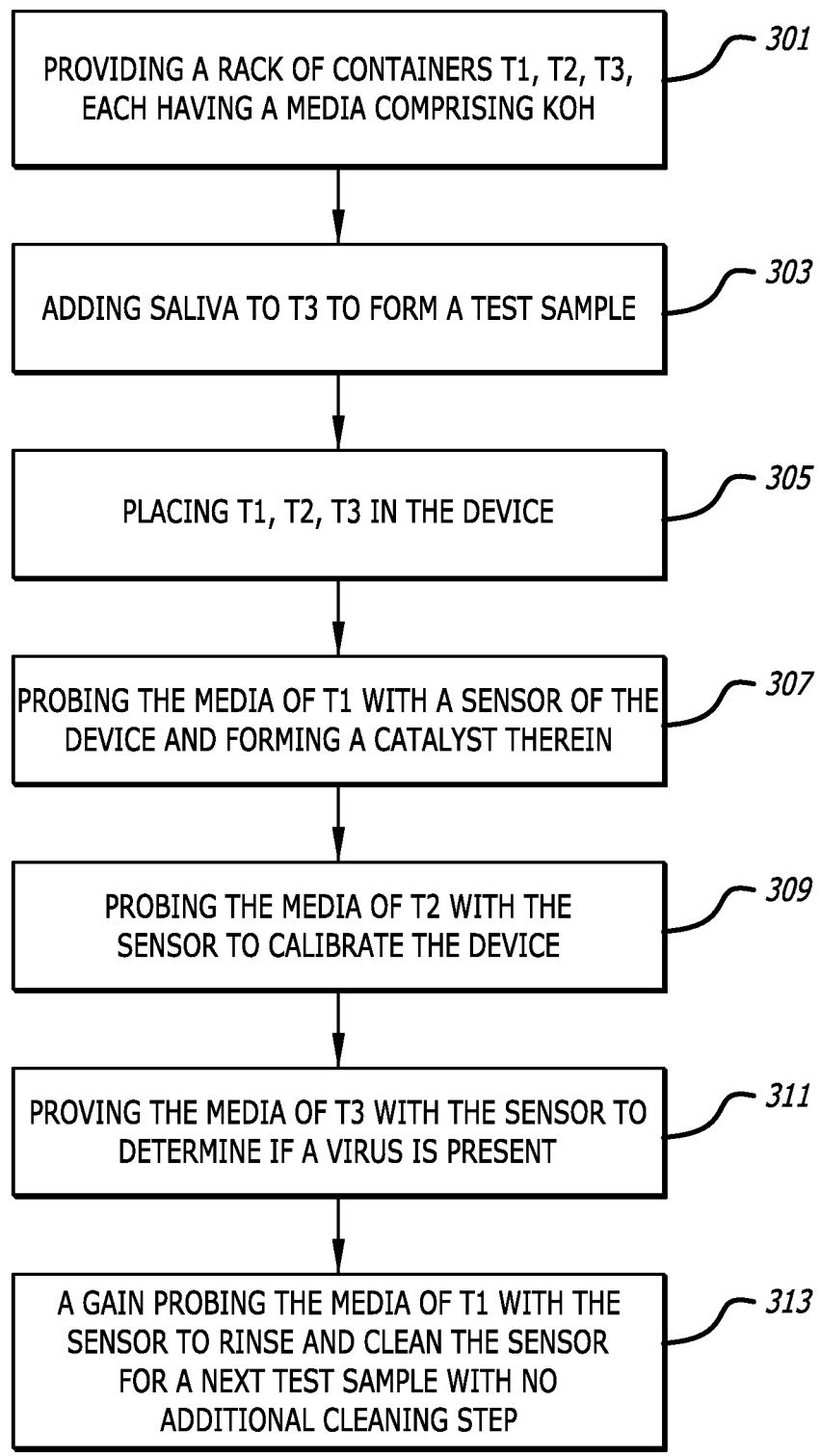
FIG. 3 is a flowchart of an embodiment of a method in accordance with this disclosure.

FIGS. 1-3 disclose embodiments of a kit for testing for a virus and interacting with a sensor. For example, in FIG. 1 the kit can include a first container (T1) having a first media for conditioning, catalyst formation and rinsing of the sensor. The first media can comprise V mL of 1 M KOH. The kit can have a second container (T2) with a second media for negative control (baseline solution) for the sensor. The second media can comprise W ML of 0.01 M KOH. The kit can further include a third container (T3) having a third media for sample testing with the sensor. The third media can comprise X mL of 0.01 M KOH. The T3 can be configured to receive Y mL of saliva to complete a Z mL total volume in the T3 prior to sample testing. In some versions, a ratio V: W: X: Y: Z=1.0: 1.0: 0.9: 0.1: 1.0 can be used. In addition, a rack R can retain and support T1, T2 and T3, in some examples, which can be color coded.

Embodiments of T1, T2 and T3 can be identical in size, and each can include a cap C to seal the respective containers. The caps C also can be colored coded to match the containers. In some versions, the virus being detected can be selected from a group consisting of coronavirus (SARS-CoV-2), Human Immunodeficiency Virus (HIV), pandemic viruses and combinations thereof.

Other embodiments of the kit can include the first container (T1) having the first media for conditioning, catalyst formation and rinsing of the sensor. The first media can comprise 2 mL of 1 M KOH. The kit can have the second container (T2) with the second media for negative control (baseline solution) for the sensor. The second media can comprise 2 ML of 0.01 M KOH. The third container (T3) can have the third media for sample testing with the sensor. The third media can comprise 1.8 mL of 0.01 M KOH. T3 can be configured to receive 0.2 mL of saliva to complete a 2.0 mL total volume in the T3 prior to sample testing. In addition, the rack R can support T1, T2 and T3. Other versions of this embodiment can include any of the features, elements and components described for other embodiments throughout this disclosure.

Still other embodiments can comprise a method of using the kit with a device 101 (FIG. 2) for testing for a virus. The device 101 is fully described in U.S. Pat. No. 11,060,995, which is incorporated herein by reference in its entirety. As shown at step 301 in FIG. 3, the method can include providing a rack R of containers T1, T2, T3, each having a media comprising KOH; adding saliva to T3 to form a test sample (step 303); placing T1, T2, T3 in the device 101 (step 305); probing the media of T1 with a sensor (S) of the device 101 and forming a catalyst therein (step 307); probing the media of T2 with the sensor S to calibrate the device (step 309); probing the media of T3 with the sensor S to determine if a virus is present (step 311); and again probing the media of T1 with the sensor S to rinse and clean the sensor S for a next test sample with no additional cleaning step (step 313).

Some versions of the method can include providing T1 comprises V mL of 1 M KOH; T2 with W ML of 0.01 M KOH; T3 with X mL of 0.01 M KOH; T3 can receive Y mL of saliva to complete a Z mL total volume in the T3 prior to sample testing, and a ratio V: W: X: Y: Z=1.0: 1.0: 0.9: 0.1: 1.0, in this example.

Examples of the method can include providing T1 with 2 mL of 1 M KOH, T2 with 2 mL of 0.01 M KOH, and T3 with 1.8 mL of 0.01 M KOH. Other examples can comprise adding a volume of saliva to T3 such that a total volume of T3 is equivalent to respective total volumes of T1 and T2. In one embodiment, the method includes removing the caps C (when appropriate) and placing the rack and T1, T2 and T3 into the device 101. The method also can comprise applying a cyclic voltage in a range of 0.2 V to 0.6 V, and/or applying a potential voltage versus a reference electrode for a time period for T2. In another example, the method can include rotating the sensor inside T2, or not rotating the sensor inside T2. For T3, the method can include applying a potential voltage versus a reference electrode for a time period. The method can further comprise rotating the sensor inside T3, or not rotating the sensor inside T3. In another variation, the method can include rotating the sensor inside T2 and T3, respectively, for a same amount of time. Another example includes applying a same potential voltage to each of T2 and T3. In one version of the final step, the method can comprise at least 1 second of immersion time in the media of T1. Further embodiments of the method can include rotating the sensor inside T1, or not rotating the sensor inside T1.

Advantageously, the method may not require or comprise any additional cleaning steps. The method does not comprise adding saliva or artificial saliva to T2, in one version.

While this disclosure presents an embodiment of potassium hydroxide (KOH) and PBS KOH mixtures as the operable electrolyte, additional electrolytes may be utilized, alone or in combination, including but not limited to: hydrochloric acid (HCL), hydrobromic acid (Hbr), hydroiodic acid (HI), nitric acid (HNO3), chloric acid (HClO3), perchloric acid (HClO4), sulfuric acid (H2SO4), sodium hydroxide (NaOH), potassium hydroxide (KOH), lithium hydroxide (LiOH), barium hydroxide (Ba(OH)2), calcium hydroxide (Ca(OH)2), sodium chloride (NaCl), potassium bromide (KBr), magnesium chloride (MgCl2) and known analogs and derivatives thereof commonly utilized for their ionization properties.

In another example, the difference between a sample current and a baseline can be the signature of the sensor, such as:

Criteria for positive: Signature at 0.01 s>(0+2%)
Criteria for negative: Signature at 0.01 s≤(0+2%)

This disclosure describes the test kits composition for the detection of SARS-CoV-2 using the Ultra-Fast Covid 19 (UFC-19) diagnostic sensor that is the subject of U.S. Pat. No. 11,060,995. The test kits can enable: (1) cleaning of testing probe before and after testing, (2) reduction of consumables required during testing, and (3) elimination of the need to add saliva and/or artificial saliva to the negative control sample T2.

The embodiments can eliminate the need to add saliva to the negative control sample for SARS-CoV-2 detection. They also can eliminate the undesirable additional "cleaning step" between the catalyst formation and baseline measurement.

Other composition/volume ratios used may require a longer testing sequence in the sensor as well as the implementation of additional consumables such as: disinfecting solution, drying of probe, adding saliva to the negative control (baseline solution), or refrigeration of the negative control samples.

The T1, T2 and T3 containers are configured to receive the sensor in the respective media. The sensor can comprise a diameter of 2 mm to 4 mm. The sample could be saliva or nasal specimen.

Other embodiments can include one or more of the following items.

1. A kit for testing for a virus and interacting with a sensor, the kit comprising:
a first container (T1) having a first media for conditioning, catalyst formation and rinsing of the sensor, and the first media comprises V mL of 1 M KOH;
a second container (T2) having a second media for negative control (baseline solution) for the sensor, and the second media comprises W ML of 0.01 M KOH;
a third container (T3) having a third media for sample testing with the sensor, the third media comprises X mL of 0.01 M KOH, and the T3 is configured to receive Y mL of saliva to complete a Z mL total volume in the T3 prior to sample testing, and a ratio V: W: X: Y: Z=1.0: 1.0: 0.9: 0.1: 1.0; and
a rack to retain and support T1, T2 and T3.

2. The kit wherein T1, T2 and T3 are identical in size, and each comprises a cap to seal the respective containers.

3. The kit wherein the virus being detected is selected from a group consisting of coronavirus (SARS-CoV-2), Human Immunodeficiency Virus (HIV), pandemic viruses and combinations thereof.

4. A kit for testing for a virus and interacting with a sensor, the kit comprising:
a first container (T1) having a first media for conditioning, catalyst formation and rinsing of the sensor, and the first media comprises 2 mL of 1 M KOH;
a second container (T2) having a second media for negative control (baseline solution) for the sensor, and the second media comprises 2 ML of 0.01 M KOH;
a third container (T3) having a third media for sample testing with the sensor, the third media comprises 1.8 mL of 0.01 M KOH, and the T3 is configured to receive 0.2 mL of saliva to complete a 2.0 mL total volume in the T3 prior to sample testing; and
a rack to support T1, T2 and T3.

5. The kit wherein T1, T2 and T3 are identical in size, and each comprises a cap to seal the respective containers.

6. The kit wherein the virus being detected is selected from a group consisting of coronavirus (SARS-CoV-2), Human Immunodeficiency Virus (HIV), pandemic viruses and combinations thereof.

7. A method of using a kit with a device for testing for a virus, the method comprising:
(a) providing a rack of containers T1, T2, T3, each having a media comprising KOH;
(b) adding saliva to T3 to form a test sample;
(c) placing T1, T2, T3 in the device;
(d) probing the media of T1 with a sensor of the device and forming a catalyst therein;
(e) probing the media of T2 with the sensor to calibrate the device;
(f) probing the media of T3 with the sensor to determine if a virus is present; and then
(g) again probing the media of T1 with the sensor to rinse and clean the sensor for a next test sample with no additional cleaning step.

8. The method wherein:
T1 comprises V mL of 1M KOH;
T2 comprises W ML of 0.01 M KOH;
T3 comprises X mL of 0.01 M KOH;
T3 is configured to receive Y mL of saliva in step (b) to complete a Z mL total volume in the T3 prior to sample testing, and a ratio V: W: X: Y: Z=1.0: 1.0: 0.9: 0.1: 1.0.

9. The method wherein step (a) comprises providing T1 with 2 mL of 1 M KOH, T2 with 2 mL of 0.01 M KOH, and T3 with 1.8 mL of 0.01 M KOH.

10. The method wherein step (b) comprises adding a volume of saliva to T3 such that a total volume of T3 is equivalent to respective total volumes of T1 and T2.

11. The method wherein step (c) comprises placing the rack and T1, T2 and T3 into the device.

12. The method wherein step (d) comprises applying a cyclic voltage in a range of 0.2 V to 0.6 V.

13. The method wherein step (e) comprises applying a potential voltage versus a reference electrode for a time period.

14. The method wherein step (e) comprises rotating the sensor inside T2.

15. The method wherein step (e) comprises not rotating the sensor inside T2.

16. The method wherein step (f) comprises applying a potential voltage versus a reference electrode for a time period.

17. The method wherein step (f) comprises rotating the sensor inside T3.

18. The method wherein step (f) comprises not rotating the sensor inside T3.

19. The method wherein steps (e) and (f) comprise rotating the sensor inside T2 and T3, respectively, for a same amount of time in each of steps (e) and (f).

20. The method wherein steps (e) and (f) comprise applying a same potential voltage in each of steps (e) and (f).

21. The method wherein step (g) comprises at least 1 second of immersion time in the media of T1.

22. The method wherein step (g) comprises rotating the sensor inside T1.

23. The method wherein step (g) comprises not rotating the sensor inside T1.

24. The method wherein the method does not comprise any additional cleaning steps.

25. The method wherein the method does not comprise adding saliva or artificial saliva to T2.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," "top", "bottom," and the like, may be used herein for ease of description to describe one element's or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated degrees or at other orientations) and the spatially relative descriptions used herein interpreted accordingly.

This written description uses examples to disclose the embodiments, including the best mode, and also to enable those of ordinary skill in the art to make and use the invention. The patentable scope is defined by the claims, and can include other examples that occur to those skilled in the art. Such other examples are intended to be within the scope of the claims if they have structural elements that do not differ from the literal language of the claims, or if they include equivalent structural elements with insubstantial differences from the literal languages of the claims.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

It can be advantageous to set forth definitions of certain words and phrases used throughout this patent document. The term "communicate," as well as derivatives thereof, encompasses both direct and indirect communication. The terms "include" and "comprise," as well as derivatives thereof, mean inclusion without limitation. The term "or" is inclusive, meaning and/or. The phrase "associated with," as well as derivatives thereof, can mean to include, be included within, interconnect with, contain, be contained within, connect to or with, couple to or with, be communicable with, cooperate with, interleave, juxtapose, be proximate to, be bound to or with, have, have a property of, have a relationship to or with, or the like. The phrase "at least one of," when used with a list of items, means that different combinations of one or more of the listed items can be used, and only one item in the list can be needed. For example, "at least one of: A, B, and C" includes any of the following combinations: A, B, C, A and B, A and C, B and C, and A and B and C.

Also, the use of "a" or "an" is employed to describe elements and components described herein. This is done merely for convenience and to give a general sense of the scope of the invention. This description should be read to include one or at least one and the singular also includes the plural unless it states otherwise.

The description in the present application should not be read as implying that any particular element, step, or function is an essential or critical element that must be included in the claim scope. The scope of patented subject matter is defined only by the allowed claims. Moreover, none of the claims invokes 35 U.S.C. § 112(f) with respect to any of the appended claims or claim elements unless the exact words "means for" or "step for" are explicitly used in the particular claim, followed by a participle phrase identifying a function.

Benefits, other advantages, and solutions to problems have been described above with regard to specific embodiments. However, the benefits, advantages, solutions to problems, and any feature(s) that can cause any benefit, advantage, or solution to occur or become more pronounced are not to be construed as a critical, required, sacrosanct or an essential feature of any or all the claims.

After reading the specification, skilled artisans will appreciate that certain features which are, for clarity, described herein in the context of separate embodiments, can also be provided in combination in a single embodiment. Conversely, various features that are, for brevity, described in the context of a single embodiment, can also be provided separately or in any sub-combination. Further, references to values stated in ranges include each and every value within that range.

What is claimed is:

1. A viral testing apparatus comprising:
   (a) a kit comprising:
      (i) a first container (T1) having a first media, wherein the first media comprises a catalyst formation solution having V mL of 1 M KOH;
      (ii) a second container (T2) having a second media, wherein the second media comprises a negative control (baseline solution) having W mL of 0.01 M KOH;
      (iii) a third container (T3) having a third media, wherein the third media comprises a sample solution having X mL of 0.01 M KOH, and the T3 receives Y mL of saliva to complete a Z mL total volume in the T3 prior to sample testing; and
      (iv) a rack to retain and support T1, T2 and T3, wherein the rack is operatively configured to connect one or more of T1, T2, and T3 to a sensor, wherein the connection of one or more of T1, T2, and T3 to the sensor initiates a test for a virus;
   (b) the saliva, wherein the third container contains the Y mL of the saliva; and
   (c) the sensor (S), wherein the sensor is connected to one or more of T1, T2, or T3, wherein the connection of one or more of T1, T2, and T3 to the sensor initiates the test for the virus.

2. The viral testing apparatus of claim 1, wherein T1, T2 and T3 are identical in size, and each comprises a cap to seal the respective containers.

3. The kit viral testing apparatus of claim 1, wherein the virus being detected is selected from a group consisting of coronavirus (SARS-CoV-2), Human Immunodeficiency Virus (HIV), and combinations thereof.

4. A viral testing apparatus comprising:
   (a) a kit comprising:
      (i) a first container (T1) having a first media, wherein the first media comprises a catalyst formation solution having 2 mL of 1 M KOH;
      (ii) a second container (T2) having a second media, wherein the second media comprises a negative control (baseline solution) having 2 mL of 0.01 M KOH;
      (iii) a third container (T3) having a third media, wherein the third media comprises a sample solution having 1.8 mL of 0.01 M KOH, and the T3 receives 0.2 mL of saliva to complete a 2.0 mL total volume in the T3 prior to sample testing; and
      (iv) a rack to support T1, T2, and T3, wherein the rack is operatively configured to connect one or more of T1, T2, and T3 to a sensor, wherein the connection of one or more of T1, T2, and T3 to the sensor initiates a test for a virus;
   (b) the saliva, wherein the third container contains the 0.2 mL of the saliva; and
   (c) the sensor (S), wherein the sensor is connected to one or more of T1, T2, or T3, wherein the connection of one or more of T1, T2, and T3 to the sensor initiates the test for the virus.

5. The viral testing apparatus of claim 4, wherein T1, T2 and T3 are identical in size, and each comprises a cap to seal the respective containers.

6. The viral testing apparatus of claim 4, wherein the virus being detected is selected from a group consisting of coronavirus (SARS-CoV-2), Human Immunodeficiency Virus (HIV), and combinations thereof.

* * * * *